United States Patent [19]
Joseph

[11] Patent Number: 6,068,816
[45] Date of Patent: May 30, 2000

[54] PROCESS FOR THE MILD REDUCTION OF GERMS IN PHARMACEUTICAL PREPARATIONS

[75] Inventor: Heinz Walter Joseph, Berg, Germany

[73] Assignee: Bionorica Arzneimittel GmbH, Neumarkt, Germany

[21] Appl. No.: 09/091,278

[22] PCT Filed: Dec. 12, 1996

[86] PCT No.: PCT/EP96/05578

§ 371 Date: Jun. 15, 1998

§ 102(e) Date: Jun. 15, 1998

[87] PCT Pub. No.: WO97/23232

PCT Pub. Date: Jul. 3, 1997

[30] Foreign Application Priority Data

Dec. 21, 1995 [DE] Germany .......................... 195 47 973

[51] Int. Cl.⁷ ................... A61L 2/18; A61L 2/04
[52] U.S. Cl. .................. 422/33; 422/1; 422/28; 422/202; 422/205; 422/209; 422/225; 422/309
[58] Field of Search .................. 422/28, 33, 1, 422/38, 198, 202, 205, 209, 224, 225, 307, 309

[56] References Cited

U.S. PATENT DOCUMENTS

| | | | |
|---|---|---|---|
| 3,868,213 | 2/1975 | Shulika et al. ........................... | 432/134 |
| 3,994,685 | 11/1976 | Lodige et al. . | |
| 4,844,933 | 7/1989 | Hsieh et al. ............................. | 426/521 |
| 4,876,802 | 10/1989 | Gergely et al. ............................. | 34/15 |
| 5,855,857 | 1/1999 | Dithmer .................................. | 422/307 |

FOREIGN PATENT DOCUMENTS

| | | |
|---|---|---|
| 0 435 302 | 7/1991 | European Pat. Off. . |
| 0 753 306 | 1/1997 | European Pat. Off. . |
| 96-233025 | 7/1995 | Hungary . |

OTHER PUBLICATIONS

K. H. Wallhäußer, Lebensmittel und Mikroorganismen, Steinkopff Verlag Darmstadt, 1990, pp. 100–101 English Translation of relevant parts of Document (1).

S. D. Holdsworth, Recent Developments in Dehydration and Canning, Food Manufacture, Nov. 1969, pp. 44,48.

"Vacuum Dryers", INOX Glatt AG Switzerland, Nov. 1995 pp. 1–6.

*Primary Examiner*—Robert J. Warden, Sr.
*Assistant Examiner*—Fariborz Moazzam
*Attorney, Agent, or Firm*—Ratner & Prestia

[57] ABSTRACT

The present invention relates to a process for degerminating drugs in a vacuum drying system comprising a multi-blade stirrer under the conditions of reduced pressure, keeping the active ingredients intact and largely destroying toxic mould fungi.

17 Claims, No Drawings

PROCESS FOR THE MILD REDUCTION OF GERMS IN PHARMACEUTICAL PREPARATIONS

This is the U.S. National Phase of PCT International Application No. PCT/EP96/05578.

BACKGROUND OF THE INVENTION

Pharmaceutical preparations such as cut or ground drugs and foods, e.g. cut or ground spice drugs, may not be degerminated in Germany and some other countries by means of highly effective methods corresponding to the state of the art. These especially include the treatment of the drug material with germ-reducing methods using ionising radiation, e.g. cobalt 60 or linear acceleration, and the chemical process of exposure to ethylene oxide gas. Even though such radiation processes for reducing germs in plant drugs or foods are among the most effective methods, national laws prohibiting their use have been passed as a result of severe concern in connection with the risk of the development of toxic substances.

Even so-called mild processes such as the hydrothermal process and the treatment with live steam may cause detrimental changes in the material to be degerminated. This is especially true for drug materals containing sensitive essential oils which may be changed with regard to both pharmacology and taste by such processes. Such a hydrothermal method also causes a loss of ingredients. For understandable reasons, all those disadvantages are undesirable. The above-mentioned disadvantages should also be avoided for ecological reasons, because the loss in active ingredient leads to increased consumption of plant material.

A particularly severe disadvantage of the hydrothermal processes lies in the fact that they are conducted a high temperatures, e.g. a saturated steam temperature between 110 and 160° C. This shows that even though drugs containing essential oils may be degerminated, they will unfortunately lose their original characteristics. In addition to a physical reduction of substances in the starting material, chemical changes occur which result in irreversible conversion or decomposition of additional ingredients of the drug material. Both the high temperatures of such hydrothermal degermination processes and radiation generate oxygen radicals which cause irreversible changes to the flavonoid and polyphenol content of the drug material. In case of exposure to ethylene oxide gas, carcinogenic interim products of the plant ingredients develop, which should be avoided in any case.

These known processes have also shown that extensive reduction of, for example, mould fungi is very difficult, because the micro-organisms form persistent spores. Due to their characteristics, such germs and their spores, respectively, tend to amplify when left standing after sterilisation at sometimes severe conditions.

The limits for the germ content of, for example, plant drugs have been defined in DAB 10 (German pharmacopoeia, Volume 10) for medicaments containing such materials. Therefore, drugs must be discarded, because they do not correspond to the strict requirements of pharmacopoeias, e.g. DAB 10, even though they would have been suitable for use under chemical or pharmaceutical aspects.

DAB 10 defines the following maximum germ content for plant drug preparations: $10^5$ for aerobes, $10^3$ for fungi and yeasts, $10^3$ for enteric bacteria, $10^1$ for E. coli. Salmonella must not be contained. Concerning plant drugs such as drug teas, the germ content of which is reduced by scalding before use, or plant drug preparations for external application, the maximum germ content according to DAB is higher, namely $10^7$ for aerobes, $10^4$ for fungi and yeasts, $10^4$ for enteric bacteria, $10^2$ for E. coli and 0 for salmonella per gram of material. Similar values are prescribed in the European Pharmacopoeia which became nationally effective on Jan. 1, 1996, and permits as much as $10^4$ for fungi intended for internal application. However, no E. coli or salmonella germs must be present. The recommendation issued by the German expert committee for drug, spice and flavouring plants of the producers of drug and spice plants for the maximum germ content are analogous to DAB 10, so that the same maximum germ contents must be observed. The Swiss pharmacopoeia (Pharmacopoeia Helvetica VII) permits a maximum germ content of $10^4$/g for yeasts, no visible moulding being permitted with regard to mould fungi. The maximum permitted content for E. coli is $10^2$/g. Salmonella should not be detectable at all.

Experience has shown that observation of the pharmacopoeia regulations or recommendations of the expert committees is very difficult without, as outlined above, reducing the active ingredient content of the drug or changing its chemical structure and pharmacological activity in an undesirable manner.

BRIEF SUMMARY OF THE INVENTION

It is the object of the invention to provide a process which permits extensive reduction of germs but retains the structure, the qualitative and quantitative effect and the content of ingredients.

DETAILED DESCRIPTION OF THE INVENTION

Therefore, in one aspect, the present invention is a process for degerminating drugs, especially drugs on plant basis, which may be ground, characterized in that degermination is conducted in a vacuum drying system comprising a multi-blade stirrer extending through the cylindrical mixing and drying chamber and having its own drive, and, if required, comprising a vapour filter, a back-purge device, a solvent condenser comprising an aftercooler and collector, a retrograde condenser and, optionally, a process, control and regulator unit, the material to be degerminated being treated in a dryer equipped with a chopper extending throughout the entire depth of the drying and mixing chamber and comprising knives rotatirng through a comb-shaped stator at a temperature of the heating jacket of 25 to 90° C., preferably 65 to 75° C. and a product temperature of 10 to 60° C., preferably, 20 to 40° C. and especially preferably 25 to 35° C., with an ethanol-water mixture containing 10 to 90 wt. %, preferably 20 to 80 wt. %, more preferably 40 to 85 wt. % and especially preferably 70 wt. % of ethanol, at a pressure of 1 to 600 mbar, preferably 10 to 200 mbar and especially preferably between 50 and 150 mbar, the weight ratio between the alcohol-water mixture and the drug being 100:90 and 50:100 respectively, to 10:90 and 100:50, respectively, a weight ratio of 50:50 being especially preferred.

The process according to the invention is further characterized in that the drug(s) to be degerminated are selected from the species of althaea, rosemarinus, juglans, millefolium, centaurium, rosmarinum, gentiana, primula, rumex, sambuco and verbena in the form of blossoms, roots or rhizomes and tubers, leaves or other parts of the plant.

Furthermore, the drug material to be degerminated is selected from the group of flos sambuci, flos primulae or herba rumicis.

Also, the plant drug material to be degerimitiated can be one of radix althaeae, folium rosmarini, folium juglandis, herba millefolii, herba centaurii or radix gentianae.

Surprisingly the inventors have now found that this object which overcomes the disadvantages of the prior art can be achieved under the following conditions, using the vacuum drying system characteriseci below. Such a drying system is known under the designation INOX-MAURER-Vakuumtrockner (vacuum dryer) offered for sale by INOX-Glatt AG of Switzerland. Analogous systems are also known under the designation Riniker-MZA-Mehrzweckanlage (multi-purpose device), cr INOX-GLATT (Maurer)-Vakuumtrockner. These vacuum drying systems are characterised in that they comprise a multi-blade stirrer extending through a cylindrical mixing and drying chamber and having its own drive, and, if required, such systems comprise a filter, a backpurge device, a solvent condenser comprising an aftercooler and collector, a retrograde condenser and/or a process, control and regulator unit. As commercially available devices, IUT-INOX-Universaltrockner (universal dryer), e.g. types IUT 20 or IUT 50, may be mentioned. When conducting the degerminating process according to the invention, the pressures are adjusted in such a manner that a pressure of 1 to 600 mbar, preferably 10 to 200 mbar and especially preferably 50 to 150 mbar is selected when evaporating the water-ethanol mixture used for degermination.

A suitable ethanol concentration in the hydroalcoholic mixture is 10 to 96%, preferably 30 to 90% or 40 to 80%, respectively. Another preferred range is 20 to 75%, a 70% concentration being especially preferred. The quantity ratio of the drug to be degerminated, which may be ground, to the ethanol-water mixture is 100:50 to 50:100.

The temperatures to be selected for drying are between 25 and 90° C. for the heating jacket, the range of 65 to 75° C. being preferred. The product temperature is controlled between 10 and 60° C., preferably 20 and 40° C. and especially preferably 25 and 35° C.

In a degermination process, cut or ground drugs, optionally for processing into drug preparations, are added to a mixture of ethanol and water, a mixture of 80% of ethanol and 20% of water or 70% of ethanol and 30% of water being especially preferred, and after exposure over several days, e.g. 2 to 15 days, are then gently treated in the above-described drying system, the parameters described above being observed.

Especially preferred quantity ratios of the drug to the ethanol-water mixture are 100:90 to 10:90 with 50:50 being especially preferred.

All percentages and ratios are based on the relevant weights.

As required and depending on the consistency of the material fed into the device for degermination the stirrer is activated.

In order to show the unexpected advantages of the degermination process according to the invention, the following table provides a number of comparative values on the basis of plant drugs commonly used. In order to illustrate the superiority of the degermination process according to the invention, comparative degermination was carried out on the basis of a drying process. For comparative purposes said drying of the drug to be treated and removal of the alcohol/water mixture, respectively, was carried out under regular pressure conditions according to the prior art. As was the case in the degermination process according to the invention, the product temperature during drying according to the prior art was between 25 and 35° C., said prior art process being carried out in a customary drying chamber.

EXAMPLE 1

Flos sambuci

EXAMPLE 2

Flos primulae

EXAMPLE 3

Herba rumicis

In the following table, the pertinent original germ values for the above examples are compared with the germ values after degermination according to the invention and sterilisation according to the prior art.

Comparative Degermination Values

| | Example | | | | | | | | |
|---|---|---|---|---|---|---|---|---|---|
| | 1) Flos sambuci | | | 2) Flos primulae | | | 3) Herba rumicis | | |
| Type of germ | Before degermination | After degermination acc. to the invention | After degermination acc. to the prior art | Before degermination | After degermination acc. to the invention | After degermination acc. to the prior art | Before degermination | After degermination acc. to the invention | After degermination acc. to the prior art |
| Aerobes and anaerobes | $10^5$ | $10^5$ | $10^5$ | $10^5$ | $10^4$ | $10^4$ | $10^6$ | $10^5$ | $10^4$ |
| Yeast | $10^3$ | $10^2$ | $10^3$ | $10^2$ | $10^2$ | $10^3$ | $10^4$ | $10^3$ | $10^3$ |
| Mould fungi | $10^3$ | $10^2$ | $10^4$ | $10^3$ | $10^3$ | $10^5$ | $10^4$ | $10^3$ | $10^5$ |
| Enteric bacteria | $10^3$ | $10^3$ | $10^2$ | $10^4$ | $10^3$ | $10^3$ | $10^5$ | $10^2$ | $10^2$ |
| E. coli | $10^2$ | $10^1$ | $10^1$ | $10^2$ | $10^1$ | $10^1$ | $10^2$ | $10^1$ | $10^1$ |
| Salmonella | 0 | 0 | 0 | 0 | 0 | 0 | 0 | 0 | 0 |

The degermination values given in the above table show with surprising clarity that the degermination process according to the invention permits compliance with the pharmacopoeia standards. This is especially true for observing the maximum values for mould fungi which are highly undesirable in food and drug preparations because of the development of hepatotoxic aflatoxins. With regard to the maximum content of *E. coli* germs, reference is made to the fact that the number of $10^1$ really means rounding off to 10 so that the values actually found were between 1 and 9. In other words, such germs would be below the detection limit in drugs made with these degerminated samples.

The results of the comparative experiments show that the degermination process according to the prior art results in such an increase of the germ number, especially of the mould fungi, that the drugs thus degerminated do not meet the standards of the pharmacopoeia and must therefore be discarded.

What is claimed is:

1. A process for degerminating plant drug material, using, a vacuum drying system comprising a multi-blade stirrer extending through a cylindrical mixing and drying chamber having its own drive, the vacuum drying system also including a vapour filter for removing vapors from the mixing and drying chamber, a back-purge device for purging the vapor filter, a solvent condenser comprising an aftercooler for vapors removed from the mixing and drying chamber and a collector for vapors removed from the mixing and drying chamber, a retrograde condenser for condensing vapors removed from the mixing and drying chamber and, a heating jacket for heating the mixing and drying chamber and the steps of;

pre-mixing the plant drug material with an ethanol-water mixture containing 10 to 90 wt. % ethanol;

establishing a ratio, by weight, between the alcohol-water mixture and the plant drug material between 100:90 and 10:90;

introducing the plant drug material and ethanol-water mixture into the mixing and drying chamber equipped with a chopper extending throughout the entire depth of the drying and mixing chamber, the chopper having knives rotating through a comb-shaped stator;

maintaining a temperature of the heating jacket between 25 and 90° C.;

maintaining a temperature between 10 and 60° C. in the material in the mixing and drying chamber; and operating the vacuum drying system at a pressure of 1 to 600 mbar, thereby degerminating said plant drug material.

2. A process according to claim 1, characterised in that the drug(s) to be degerminated are selected from species of althaea, rosemarinus, juglans, millefolium, centaurium, rosmarinum gentiana, primula, rumex, sambuco and verbena in the form of blossoms, roots or rhizomes and tubers, leaves or other parts of the plant.

3. A process according to claim 1, including selecting the drug material to be degerminated from the group consisting of flos sambuci, flos primulae and herba rumicis.

4. A process according to claim 1, including selecting the plant drug material from the group consisting of radix althaeae, folium rosmarini, folium juglandis, herba millefolii, herba centaurii and radix gentianae.

5. A process according to claim 1 wherein the temperature of the heating jacket is between 65 ° and 75° C.

6. A process according to claim 1 wherein the product temperature is between 20° and 40° C.

7. A process according to claim 1 wherein the product temperature is between 25° and 35° C.

8. A process according to claim 1 wherein the ethanol-water mixture contains from 20 to 80 wt. % ethanol.

9. A process according to claim 1 wherein the ethanol-water mixture contains 70 wt. % ethanol.

10. A process according to claim 1 wherein the pressure is between 10 and 200 mbar.

11. A process according to claim 1 wherein the pressure is between 50 and 150 mbar.

12. A process according to claim 1 wherein the weight ratio between the alcohol-water mixture and the drug is 50:50.

13. A process according to claim 2 including selecting said plant drug material to be degerminated from the group consisting of flos sambuci, flos primulae and herba rumicis.

14. A process according to claim 2 including selecting said plant drug material from the group consisting of radix althaeae, folium rosmarini, folium jugandis, herba millefolii, herba centaurii and radix gentianae.

15. A process according to claim 3 including selecting said plant drug material from the group consisting of radix althaeae, folium rosmarini, folium juglandis, herba millefolii, herba centaurii and radix gentianae.

16. A process according to claim 1 including using a process control and regulation unit with said vacuum drying system.

17. A process for degermninating plant drug material comprising:

(a) mixing the plant drug material to be degerminated with an ethanol-water mixture containing 10 to 90% by weight, ethanol;

(b) maintaining said plant drug material and ethanol water mixture for a period of from 2 to 15 days;

introducing said plant drug material and ethanol-water mixture from step (b) into a vacuum drying system having a drying and mixing chamber containing a chopper, the chopper extending throughout the entire depth of the drying and mixing chamber, the chopper consisting of knives rotating through a comb-shaped stator;

maintaining the drug material and ethanol-water mixture at a temperature of from 10° to 60° C. and at a pressure of fromn 1 to 600 mbar for a time sufficient to complete the degermination of the plant drug material.

* * * * *

UNITED STATES PATENT AND TRADE MARK OFFICE
CERTIFICATE OF CORRECTION

PATENT NO. : 6,068,816
DATED : May 30, 2000
INVENTOR(S) : Heinz Walter Joseph

It is certified that error appears in the above-identified patent and that said Letters Patent is hereby corrected as shown below:

Column 1, line 25, delete the word "materals" and substitute therefor --materials--.

Column 2, line 46, delete the word "rotatirng" and substitute therefor --rotating--.

Column 3, line 1, delete the word "degerimitiated" and substitute therefor --degerminated--.

Column 3, line 7, delete the word "characteriseci" and substitute therefor --characterised--.

Column 3, line 12, delete "cr" and substitute therefor --or--.

Column 6, line 25, delete the word "jugiandis" and substitute therefor --juglandis--.

Column 6, line 50, delete the word "fromn" and substitute therefor --from--.

Signed and Sealed this

Twenty-seventh Day of March, 2001

*Attest:*

NICHOLAS P. GODICI

*Attesting Officer*  Acting Director of the United States Patent and Trademark Office